United States Patent
Matsui et al.

(10) Patent No.: US 9,233,065 B2
(45) Date of Patent: Jan. 12, 2016

(54) METHOD FOR PRODUCTION OF RESIN PARTICLE

(75) Inventors: Hideki Matsui, Himeji (JP); Yoshiki Nakaie, Himeji (JP); Hajime Komada, Himeji (JP)

(73) Assignee: DAICEL-EVONIK LTD., Tokyo (JP)

( * ) Notice: Subject to any disclaimer, the term of this patent is extended or adjusted under 35 U.S.C. 154(b) by 247 days.

(21) Appl. No.: 12/663,147

(22) PCT Filed: May 22, 2008

(86) PCT No.: PCT/JP2008/059856
§ 371 (c)(1),
(2), (4) Date: Dec. 4, 2009

(87) PCT Pub. No.: WO2008/149755
PCT Pub. Date: Dec. 11, 2008

(65) Prior Publication Data
US 2010/0178309 A1    Jul. 15, 2010

(30) Foreign Application Priority Data
Jun. 5, 2007    (JP) ................ 2007-149523

(51) Int. Cl.
| | |
|---|---|
| *A61K 8/88* | (2006.01) |
| *A61K 8/11* | (2006.01) |
| *A61K 8/27* | (2006.01) |
| *A61Q 19/00* | (2006.01) |
| *A61Q 17/04* | (2006.01) |
| *C08J 3/12* | (2006.01) |

(Continued)

(52) U.S. Cl.
CPC ... *A61K 8/88* (2013.01); *A61K 8/11* (2013.01); *A61K 8/27* (2013.01); *A61K 8/29* (2013.01);
(Continued)

(58) Field of Classification Search
CPC ............. A61K 8/88; A61K 8/11; A61K 8/27; A61K 8/29; A61K 2800/413; A61K 2800/412; A61Q 19/00; A61Q 17/04; C08J 3/12; C08J 2377/00; B82Y 5/00
See application file for complete search history.

(56) References Cited

U.S. PATENT DOCUMENTS

| | | | |
|---|---|---|---|
| 6,599,520 B2 * | 7/2003 | Scarborough et al. | ........ 424/426 |
| 2002/0022883 A1 * | 2/2002 | Burg | ................................ 623/8 |

(Continued)

FOREIGN PATENT DOCUMENTS

| | | |
|---|---|---|
| JP | 61-9433 A | 1/1986 |
| JP | 6-63387 A | 3/1994 |

(Continued)

OTHER PUBLICATIONS

Supplementary European Search Report, dated Aug. 2, 2011, for European Application No. 08764825.9.

*Primary Examiner* — Trevor Love
(74) *Attorney, Agent, or Firm* — Birch, Stewart, Kolasch & Birch, LLP (57) ABSTRACT

Disclosed is a method for producing resin particles, which can impart a desired function to the surface of resin particles efficiently and simply. Also disclosed are resin particles produced by the method.

The method produces resin particles by melting and mixing an acidic-group-containing thermoplastic resin or elastomer with filler particles and a water-soluble material to give a resin composition containing resin fine particles formed by the thermoplastic resin and the filler particles and dispersed in a matrix including the water-soluble material; and removing the matrix component from the resin composition, to give the resin particles. The resulting resin particles each include a core particle including the acidic-group-containing thermoplastic resin or elastomer, and the filler particles immobilized on the outside of the core particle. The acidic group is preferably carboxyl group or carboxylic anhydride group.

9 Claims, 3 Drawing Sheets

(51) Int. Cl.
  *B82Y 5/00*  (2011.01)
  *A61K 8/29*  (2006.01)
(52) U.S. Cl.
  CPC . *A61Q 19/00* (2013.01); *B82Y 5/00* (2013.01); *C08J 3/12* (2013.01); *A61K 2800/412* (2013.01); *A61K 2800/413* (2013.01); *A61Q 17/04* (2013.01); *C08J 2377/00* (2013.01)

(56) References Cited

U.S. PATENT DOCUMENTS

| | | |
|---|---|---|
| 2005/0079506 A1 | 4/2005 | Leon et al. |
| 2005/0186423 A1* | 8/2005 | Johnson et al. ............... 428/403 |
| 2005/0218551 A1 | 10/2005 | Halahmi et al. |
| 2005/0234154 A1 | 10/2005 | Halahmi |
| 2005/0250052 A1 | 11/2005 | Nguyen |
| 2007/0125266 A1 | 6/2007 | Ito |

FOREIGN PATENT DOCUMENTS

| | | |
|---|---|---|
| JP | 9-165457 A | 6/1997 |
| JP | 10-176065 A | 6/1998 |
| JP | 2001-199836 A | 7/2001 |
| JP | 2005-29766 A | 2/2005 |
| JP | 2005-330432 A | 12/2005 |
| KR | 10-2006-0116839 A | 11/2006 |
| WO | WO 2004/033720 A2 | 4/2004 |

* cited by examiner

METHOD FOR PRODUCTION OF RESIN PARTICLE

TECHNICAL FIELD

The present invention relates to a method for the production of resin particles that will be incorporated typically into coating materials, cosmetics, and toners.

BACKGROUND ART

An exemplary method for producing resin particles is a method of heating, melting, and mixing a thermoplastic resin with another resin incompatible (immiscible) with the thermoplastic resin, and washing the resulting article with a solvent to give thermoplastic resin particles (see, for example, Japanese Unexamined Patent Application Publication (JP-A) No. S61(1986)-9433). Independently, Japanese Unexamined Patent Application Publication (JP-A) No. 2001-199836 discloses a cosmetic including an inorganic filler or a colorant. The publication describes that the cosmetic is prepared as a polymer by melting and kneading a resin for constituting a powder, a medium (another resin) for dispersing the former resin, and an inorganic pigment; and that the resulting polymer is a powdery article containing the inorganic pigment therein.

Such fine particles each including a resin powder and an inorganic pigment contained in the resin powder are generally produced by compounding the inorganic pigment into a resin material to be powdered, to give a compound; and melting and kneading the compound with a medium resin. Independently, fine particles of another type (outer-bearing fine particles) have received attention, because they can readily exhibit a high-value-added function which an inorganic fine particle inherently has. Such outer-bearing fine particles each include a resin fine particle and an inorganic pigment (inorganic microparticle) immobilized on the outside of the resin fine particle.

Patent Document 1: Japanese Unexamined Patent Application Publication (JP-A) No. S61(1986)-9433
Patent Document 2: Japanese Unexamined Patent Application Publication (JP-A) No. 2001-199836

DISCLOSURE OF INVENTION

Problems to be Solved by the Invention

An object of the present invention is to provide a method for the production of resin particles, which method imparts a desired function or activity to the surface of resin particles efficiently in a simple and easy manner. Another object of the present invention is to provide resin particles produced by the method.

Means for Solving the Problems

After intensive investigations to achieve the objects, the present inventors have found that resin fine particles having a core-shell structure can be efficiently produced in a simple and easy manner by using a thermoplastic resin having a specific functional group in combination with inorganic particles. The thermoplastic resin having a specific functional group satisfactorily interacts with the surface of the inorganic particles to give the core-shell structure including a core and a shell covering the core, in which the core is formed from the thermoplastic resin and the shell is formed from the inorganic particles. They have also found that this technique imparts a desired property (function) with high activity to resin particles. The present invention has been made based on these findings.

Specifically, the present invention provides, in an embodiment, a method for the production of resin particles. This method includes the steps of melting and mixing a thermoplastic resin or elastomer having one or more acidic groups with filler particles and a water-soluble material to form a resin composition, where the resin composition includes a matrix and resin fine particles dispersed in the matrix, the resin fine particles formed from the thermoplastic resin or elastomer and the filler particles, and the matrix is formed from the water-soluble material; and removing the matrix component from the resin composition to give the resin particles. In this method, the amount of the acidic groups in the thermoplastic resin or elastomer before mixing and kneading step is 5 mmol/kg or more based on the total amount of the thermoplastic resin or elastomer, and the resulting resin particles each include a core particle formed from the thermoplastic resin or elastomer, and the filler particles immobilized on the surface of the core particle.

The acidic groups are preferably selected from carboxyl groups and carboxylic anhydride groups. The thermoplastic resin or elastomer having one or more acidic groups is preferably selected from polyamide resins and polyamide elastomers. In the method, for example, the filler particles may have a diameter (particle size) of 0.001 to 100 μm, and the resin particles may have a diameter (particle size) of 0.01 to 500 μm. The filler particles preferably have been treated with a surface treating agent having a basic group.

In another embodiment, the present invention provides resin particles produced by the method according to the present invention. In addition, the present invention provides a cosmetic containing the resin particles according to the present invention.

Advantages

The method according to the present invention enables efficient and simple production of resin particles bearing inorganic particles on their surface, by preparing a resin composition (resin dispersion) including a matrix of a water-soluble material, and resin fine particles dispersed in the matrix, and removing the water-soluble material from the resin composition. The method can impart one or more desired properties to resin particles in a simple and easy manner and thereby enables efficient production of such resin particles usable in a wide variety of applications.

BEST MODES FOR CARRYING OUT THE INVENTION

A method for the production of resin particles, according to an embodiment of the present invention, is a method for the production of resin particles each including a core particle containing a thermoplastic resin or elastomer having one or more acidic groups, and inorganic particles immobilized or attached on the surface of the core particle.

The acidic groups may be contained in either or both of a principal chain and a side chain in the molecular structure of the thermoplastic resin or elastomer. The thermoplastic resin or elastomer having one or more acidic groups may be a single polymer, or a polymer alloy or polymer blend containing at least one polymer having one or more acidic groups. In the latter case, the polymer alloy or polymer blend may include only a polymer or polymers having one or more acidic groups or may be a mixture including a polymer or polymers having one or more acidic groups and another polymer or polymers having no acidic group.

Examples of the acidic groups include carboxyl group, sulfonic group, and phosphate group; as well as equivalents to these groups, such as carboxylic anhydride group. Among them, carboxyl group and carboxylic anhydride group are particularly preferred as the acidic group.

Examples of the thermoplastic resin include, but are not limited to, polycondensation resins containing an acidic group-containing compound as a monomer component, such as polyamides, polyesters, polyurethane, polyarylates, poly(phenylene sulfide)s, polysulfones, and poly(ether sulfone)s; styrenic resins containing styrene as a main monomer; acrylic resins typically containing a (meth)acrylic ester or acrylonitrile as a main monomer; olefinic resins containing an olefin as a main monomer; vinyl resins including vinyl chloride resins containing vinyl chloride as a main monomer, poly(vinyl alcohol) resins containing vinyl alcohol as a main monomer, and fluorocarbon resins typically containing tetrafluoroethylene as a main monomer; and other resins such as polyether resins, cellulose resins, polycarbonates, poly(phenylene ether)s, and poly(ether ether ketone)s.

The polyamide resins can be any of polyamides including polyamides as polycondensates between a diamine component (e.g., an alkylenediamine having 4 to 10 carbon atoms, such as hexamethylenediamine) and a dicarboxylic acid component (e.g., an alkylenedicarboxylic acid whose alkylene moiety having 4 to 20 carbon atoms, such as adipic acid); polyamides as polycondensates of an aminocarboxylic acid (e.g., an aminocarboxylic acid having 4 to 20 carbon atoms, such as ω-aminoundecanoic acid); polyamides as ring-opening polymerization products of a lactam (e.g., a lactam having 4 to 20 carbon atoms, such as ω-laurolactam); polyester amides as polycondensates among a diamine component (e.g., an alkylenediamine whose alkylene moiety having 4 to 10 carbon atoms, such as hexamethylenediamine), a dicarboxylic acid component (e.g., an alkylenedicarboxylic acid having 4 to 20 carbon atoms, such as adipic acid), and a diol component (e.g., an alkylenediol having 2 to 12 carbon atoms, such as ethylene glycol). Such polyamide resins include homopolyamides and copolyamides. Representative examples of polyamide resins include aliphatic polyamides such as polyamide 46, polyamide 6, polyamide 66, polyamide 612, polyamide 610, polyamide 910, polyamide 912, polyamide 1212, polyamide 1012, polyamide 1010, polyamide 11, polyamide 12, polyamide 6T, and polyamide 9; aromatic polyamides such as aramid resins; and copolyamide resins.

The polyester resins can be any of polyesters including polyesters as polycondensates between a diol component and a dicarboxylic acid component; polyesters as polycondensates of an oxycarboxylic acid; polyesters as ring-opening polymerization products of a lactone; and polyesters containing urethane bonds and prepared through a reaction between a polyester-diol and a diisocyanate. Such polyester resins include homopolyesters and copolyesters. Representative exemplary polyester resins include aliphatic polyesters such as polycaprolactones and poly(lactic acid)s; and aromatic polyesters such as poly(ethylene terephthalate)s and poly(butylene terephthalate)s.

The thermoplastic resins also include polyurethane resins. Exemplary urethane resins include resins as reaction products among a diisocyanate, a polyol, and, where necessary, a chain extender such as ethylene glycol or ethylenediamine. Representative urethane resins include urethane resins prepared from a soft segment and a hard segment. The soft segment may include, for example, a polyester-diol, a polyether-diol, or a polycarbonate-diol. The hard segment may include, for example, an isocyanate (e.g., diphenylmethane diisocyanate (MDI), toluene diisocyanate (TDI), isophorone diisocyanate (IPDI), hydrogenated diphenylmethane diisocyanate (hydrogenated MDI), Or hexamethylene diisocyanate (HDI)), a low-molecular-weight diamine, or a glycol.

Exemplary styrenic resins include styrenic polymers such as polystyrenes and α-methylstyrene polymers; copolymers of styrene or a derivative thereof typically with (meth)acrylic acid, a (meth)acrylic ester, or acrylonitrile; and resins derived from these resins with the incorporation of a rubber component, such as high-impact polystyrene (HIPS) resins and acrylonitrile-butadiene-styrene (ABS) resins. Exemplary acrylic resins include poly((meth)acrylic acid)s; poly(alkyl (meth)acrylate)s such as poly(methyl (meth)acrylate)s and poly(ethyl (meth)acrylate)s; polyacrylonitriles; and copolymers corresponding to them. Exemplary olefin resins include polyethylenes, polypropylenes, polybutenes, ethylene-propylene copolymers, and ethylene-acrylic acid copolymers. Exemplary vinyl resins include homopolymers or copolymers of vinyl compounds such as vinyl acetate, vinyl chloride, vinylidene chloride, and ethylene-vinyl acetate; as well as polyvinyl alcohol)s, fluorocarbon resins, and vinyl ester resins. Exemplary cellulose derivatives include cellulosic homopolymers or copolymers.

Exemplary polyolefinic resins include polyethylenes, polypropylenes, ethylene-propylene copolymers, ethylene-(meth)acrylic acid copolymers, ethylene-(meth)acrylic ester copolymers, and ethylene-vinyl acetate copolymers. Exemplary (meth)acrylic resins include poly(methyl methacrylate)s and methyl methacrylate-acrylic ester copolymers. Exemplary styrenic resins include polystyrenes and styrene-(meth)acrylic ester copolymers. Exemplary vinyl resins include vinyl chloride resins.

Exemplary polyether resins include poly(ethylene glycol)s, poly(ethylene oxide)s, and polyoxymethylenes. Exemplary cellulose resins include cellulose esters such as cellulose acetate, cellulose acetate butyrate, and hydroxyethyl cellulose; cellulose ethers; and cellulose carbamates. Exemplary polycarbonate resins include aromatic polycarbonates containing, for example, bisphenol-A; and aliphatic polycarbonates containing, for example, 1,6-hexamethylene glycol.

Examples of the elastomer include so-called rubbers and thermoplastic elastomers. Exemplary rubbers include isoprene rubbers (IR), butadiene rubbers (BR), chloroprene rubbers (CR), styrene-butadiene rubbers (SBR), nitrile rubbers (acrylonitrile-butadiene rubbers; NBR), butyl rubbers (isobutylene-isoprene rubbers; IIR), ethylene-propylene rubbers [e.g., ethylene-propylene copolymers (EPM) and ternary ethylene-propylene rubbers (EPDM)], acrylic rubbers (e.g., copolymers of ethyl acrylate and a comonomer (ACM), and ethyl acrylate-acrylonitrile copolymers (ANM)), epichlorohydrin rubbers, silicone rubbers, fluorocarbon rubbers (FKM), urethane rubbers (e.g., polyester-urethane rubbers; AU), and chlorosulfonylpolyethylenes (CSM). Such rubbers may be either unvulcanized or vulcanized.

The thermoplastic elastomers can be known elastomers each having a hard segment and a soft segment per molecule. Examples thereof include thermoplastic polyamide elastomers (TPAE), thermoplastic polyester elastomers (TPEE), thermoplastic polyurethane elastomers (TPU), thermoplastic polystyrene elastomers (TPS), thermoplastic fluorocarbon polymer elastomers, and thermoplastic polyolefin elastomers (TPO). Exemplary thermoplastic polyamide elastomers include polyamide elastomers each containing a polyamide component (e.g., polyamide 6 or polyamide 12) and a polyether component (e.g., a polyether-diol) as a hard segment and a soft segment, respectively.

Among them, preferred are water-insoluble resins such as polyamide resins, thermoplastic polyamide elastomers, (meth)acrylic resins, styrenic resins, and polyurethane resins, of which polyamide resins and thermoplastic polyamide elastomers are typically preferred.

Exemplary processes for introducing acidic groups into a thermoplastic resin or elastomer include (A) a process of copolymerizing a main monomer component with a polymerizable compound having at least one acidic group as a comonomer; (B) a process of reacting a thermoplastic resin having a reactive functional group with a compound having both at least one acidic group (e.g., any of the above-mentioned acidic groups) and a functional group reactive with the reactive functional group; and (C) a process of carrying out polymerization while using an acidic-group-containing component as a monomer component for the formation of a polycondensate resin, where the acidic-group-containing component is used in an excess amount exceeding the stoichiometric ratio. The introduction may be performed from a process suitably chosen according to the type of the thermoplastic resin.

The process (A) is, for example, suitable for introducing acidic groups typically into vinyl resins and elastomers. Specifically, an olefinic resin having one or more acidic groups can be prepared by carrying out copolymerization of an olefin as a main monomer with, as a comonomer, a polymerizable unsaturated compound having one or more acidic groups, such as acrylic acid, methacrylic acid, fumaric acid, maleic acid, maleic anhydride, itaconic acid, or β-carboxyethyl acrylate (β-CEA). A urethane resin having one or more acidic groups can be prepared by carrying out polycondensation of a polyol and a polyisocyanate as main monomers with, as a comonomer, a polycondensable compound having one or more acidic groups, such as dihydroxypropionic acid, or caprolactone adduct or ethylene oxide adduct thereof.

The process (B) is suitable for the introduction of acidic groups into thermoplastic resins each having a reactive functional group in principal chain or side chain; and into thermoplastic resins which have been prepared by copolymerizing a main monomer component with, as a comonomer, a polymerizable unsaturated compound having a reactive functional group. The compound having both at least one acidic group (e.g., any of the above-mentioned acidic groups) and a functional group reactive with the reactive functional group can also be such a compound that gives the functional group and acidic group(s) during the reaction process, such as an acid anhydride. Exemplary combinations of the reactive functional group with the compound include the combination of hydroxyl group with an acid anhydride; and the combination of amino group with an acid anhydride. Specifically, by taking a reaction between a hydroxyl-containing thermoplastic resin and an acid anhydride as an example, the reaction may be carried out, for example, by copolymerizing a main monomer component with, as a comonomer, a hydroxyl-containing monomer, such as 2-hydroxyethyl acrylate (HEA) or 2-hydroxyethyl methacrylate (HEMA), to give a copolymer, and reacting the copolymer with an acid anhydride such as succinic anhydride or trimellitic anhydride.

Representative examples of the thermoplastic resins each having hydroxyl group in principal chain or side chain include aromatic and aliphatic polycarbonates each prepared through polycondensation of a dihydroxy compound (e.g., bisphenol-A or 1,6-hexamethylene glycol) and phosgene or through transesterification between the dihydroxy compound and a carbonic acid ester; cellulosic resins such as cellulose acetate, cellulose acetate butyrate, and hydroxyethyl cellulose; and urethane resins each prepared through a reaction between a polyisocyanate and a polyol mainly containing glycol. Exemplary polyols mainly containing glycol include polyester diols, polyether dials, and polycarbonate diols. Exemplary polyisocyanates include MDI, TDI, IPDI, hydrogenated MDI, and HDI.

The process (C) is suitable for the introduction of acidic groups into polycondensate resins each prepared through polycondensation using an acidic-group-containing compound as a monomer component. Specifically, a polyamide having carboxyl groups mainly at its terminals can be prepared by carrying out a polycondensation reaction using a dicarboxylic acid in excess to a diamine component.

The amount of acidic groups (the amount of terminal acidic groups) may be 5 mmol/kg or more (e.g., from 5 to 1000 mmol/kg) based on the total amount of the thermoplastic resin. The amount of acidic groups is preferably from about 5 to about 500 mmol/kg, and especially preferably from about 10 to about 350 mmol/kg, though it is selectable within a range not adversely affecting inherent properties of the thermoplastic resin or elastomer. The thermoplastic resins for use herein have specific amounts of acidic groups and thereby enable filler particles to be immobilized or anchored on the outside of core particles formed from the thermoplastic resins. This efficiently imparts one or more superior functions or activities to the resulting resin particles even when the filler particles are used in small amounts.

Representative examples of the thermoplastic resin or elastomer having one or more acidic groups include "DAIAMID L1600" supplied as a polyamide 12 by Daicel-Degussa Ltd.; and "DAIAMID E62" supplied as a polyamide elastomer by Daicel-Degussa Ltd.

The filler particles herein can be inorganic or organic fillers in the form of particles. As used herein a "filler" refers to a substance that is relatively inactive and imparts a various functions or properties to the thermoplastic resin. Examples of the functions or properties include insulating properties, strength, viscous properties, incombustibility (flame resistance), electroconductivity, brightness, coloring properties, and antimicrobial activities. Such fillers include inorganic fillers and organic fillers. Exemplary inorganic fillers include calcium carbonate, magnesium carbonate, clay, kaolin, calcium phosphate, hydroxyapatite, mica, talc, silica, quartz powder, glass powder, diatomaceous earth, nepheline syenite, cristobalite, wollastonite, aluminum hydroxide (for imparting incombustibility), iron oxide, zinc oxide, titanium oxide, aluminum oxide (alumina), calcium sulfate, barium sulfate, dolomite, silicon carbide, silicon nitride, boron nitride, metallic powders, graphite, and carbon black (for imparting, for example, electroconductivity). In addition, antimicrobial fillers can also be used herein. Such antimicrobial fillers contain compounds combined with metal ions having an antimicrobial function, such as silver, copper, and zinc ions; and examples thereof include silver-hydroxyapatite and silver-zeolite. Exemplary organic fillers include granules of polymers such as crosslinked poly(methyl methacrylate)s.

Among such fillers, inorganic or organic colorants are preferably used, because they develop clear colors as a result of immobilization to the surface of the thermoplastic resin core particles. Exemplary inorganic colorants include inorganic pigments such as carbon black, titanium oxide, ultramarine blue pigment, iron oxide red, black iron oxide, yellow iron oxide, chromium oxide, and multicomponent oxide pigments. Exemplary organic colorants include organic pigments including azo pigments; polycyclic pigments such as anthraquinone, copper phthalocyanine blue, copper phthalocyanine green, quinacridone, and diketopyrrolopyrrole pigments; as well as disperse dyes and fat dyes for use in resins. Also preferred are tar dyes (tar colors) for use typically in cosmetics and specified in the Ministry of Health and Welfare Ordinance No. 30 of 1966; and lake pigments such as aluminum lakes.

Such filler particles may have undergone a treatment typically with a surface treating agent. Exemplary surface treating agents usable herein include silane coupling agents. When the thermoplastic resin has carboxyl group as the acidic group, a surface treatment of the filler particles with a surface treating agent having a basic group (e.g., an aminosilane coupling agent) is very effective so as to provide a strong interaction between the thermoplastic resin and the filler particles.

The shape of filler particles is not especially limited, as long as being a particle form and can be any of, for example, spherical, spheroid (ellipsoid), cylindrical (round columnar) and rectangular columnar shapes. The dimensions (size) of the particles can be chosen according to the intended use within a range not adversely affecting dispersibility of the filler particles. For example, the diameter or major axis of the filler particles is typically from about 0.001 to about 100 µm, preferably from about 0.005 to about 50 µm, and more preferably from about 0.010 to about 30 µm.

The amount of the filler particles is, for example, typically from about 1 to about 80 parts by weight and preferably from about 5 to about 60 parts by weight, per 100 parts by weight of the thermoplastic resin or elastomer having one or more acidic groups.

Resin particles according to an embodiment of the present invention may further contain additives in addition to the thermoplastic resin or elastomer having one or more acidic groups, and the filler particles. Regular additives such as antioxidants, lubricants, and weather stabilizers are suitably usable herein. The types and amounts of such additives can be appropriately chosen according to required properties of the resin particles.

A method according to an embodiment of the present invention produces resin particles by melting and mixing a thermoplastic resin or elastomer having one or more acidic groups (hereinafter also briefly referred to as "thermoplastic resin") with filler particles and a water-soluble material to form a resin composition (resin dispersion) containing resin fine particles dispersed in a matrix, where the resin fine particles are formed from the thermoplastic resin and the filler particles, and the matrix is formed from the water-soluble material; and removing the matrix component from the resin composition.

The water-soluble material can be any known material without limitation, as long as being incompatible (immiscible) with the resin fine particles. Among such water-soluble materials, preferred are water-soluble materials that will melt or soften when or to be kneaded with the thermoplastic resin at a temperature at which the thermoplastic resin melts or softens (for example, at a temperature of from 100° C. to 300° C.). Exemplary water-soluble materials include saccharides such as monosaccharides, oligosaccharides, polysaccharides, sugar alcohols, polydextroses, maltodextrins, and inulins; hydrates and hydrolysates of these saccharides; polyethylene oxides; polyethylene glycols; poly(vinyl alcohol)s; and cellulose derivatives. Of such water-soluble materials, preferred are those having a viscosity as low as possible when dissolved in a disperse medium such as water, because such materials are easy to be removed after the process.

When "a water-soluble material is incompatible with resin fine particles", it may be verified by the occurrence of the following phenomenon (i) or (ii). Specifically, (i) when a thermoplastic resin having acidic groups, filler particles, and a water-soluble material are melted and kneaded to give a resin composition, the resin composition shows a melting point or glass transition point near (e.g., within ±20%) to the melting point or glass transition point of the thermoplastic resin alone or that of the water-soluble material alone. Alternatively, (ii) when a mixture containing a water-soluble material and about 20 percent by weight of a thermoplastic resin having acidic groups is heated, kneaded, and cooled, and the resulting kneadate is dissolved in water to give a dispersion, the dispersion is observed under microscopic observation as a dispersion which contains particles of the thermoplastic resin having acidic groups dispersed in the matrix water-soluble material. The glass transition points can be measured according to a common process such as differential scanning calorimetry (DSC) or dynamic viscoelastic measurement.

The resin composition herein contains a matrix and resin fine particles dispersed in the matrix, in which the resin fine particles contain the resin, and the matrix contains the water-soluble material. Such resin composition can be prepared according to a known procedure. For example, the resin composition can be prepared by molding the resin into particles (resin particles) and dispersing the resin particles in the water-soluble material; or by melting and kneading the thermoplastic resin and water-soluble material with each other, and extruding the kneadate. The resin composition for use herein is preferably one prepared according to the latter procedure.

In a preferred embodiment, a resin composition is prepared, for example, by melting and kneading a water-insoluble thermoplastic resin or elastomer having one or more acidic groups, filler particles, a water-soluble material, and, where necessary, additives with one another to give a dispersion which includes fine particles formed from the water-insoluble thermoplastic resin having substantially the same dimensions and having spheroid shapes (preferably spherical shapes) dispersed therein; and extruding the dispersion. The melting/kneading and extrusion can be performed by using any of regular kneading machines (kneaders) and extruders (e.g., single-screw extruders, twin-screw extruders, and roll extruders).

The kneading and extruding temperatures are not critical, as long as being equal to or higher than the melting temperatures of the components and equal to or lower than the upper temperature limits (heatproof temperatures) of the components. The temperatures are appropriately chosen according to the types and amounts of the water-soluble material and thermoplastic resin and are, for example, from about 100° C. to about 300° C., and preferably from about 110° C. to about 250° C. The viscosity of the resin composition upon extrusion preferably ranges from 1 to 10000 pascal-seconds (Pa·s) in terms of melt viscosity at the extrusion temperature measured with a capillograph. The melt viscosity plays an important role in the control of the particle diameter of resin particles dispersed in the water-soluble material, which resin particles include the thermoplastic resin having one or more acidic groups and the filler particles. The melt viscosity can be adjusted by suitably selecting the types of the water-soluble material and thermoplastic resin. The resin composition may be extruded into articles of any shape such as strands or sheets. The extrudate is preferably immediately cooled after the extrusion.

The above process gives a resin composition which include a matrix formed from the water-soluble material and, dispersed therein, fine particles containing the thermoplastic resin and filler particles. Where necessary, the resin composition may be subjected to a common forming/processing process such as melting, drawing, and/or compressing.

The method according to the present invention produces resin particles by removing the water-soluble material from the resin composition having the above structure. The removal of the water-soluble material may be performed, for example, through a washing step of the resin composition, in which the resin composition is dispersed in a solvent to dissolve the water-soluble material in a liquid phase, and the resin fine particles as a solid phase are recovered. Exemplary solvents usable herein include water; water-soluble (water-miscible) organic solvents such as lower alcohols; and mixtures of these solvents. Among them, water is preferably used because it is environmentally friendly and easy to handle.

The dispersion can be performed using a common mixing/stirring device such as stirrer or ultrasonic generator. Among them, an ultrasonic generator is advantageously used so as to improve dispersion efficiency and to shorten the processing time.

The resin fine particles recovered through the washing step is dried to give product resin particles. The size of the resulting resin particles is, for example, from about 0.01 to about 500 μm, preferably from about 0.01 to about 100 μm, and especially preferably from about 0.5 to about 80 μm, though it is not critical and can be chosen suitably according to the intended use of the resin particles. The size of the fine particles (resin particles) can be controlled, for example, by adjusting the types and amounts (ratio between amounts) of the water-soluble material and thermoplastic resin, the structure of the extruder, and conditions for extrusion.

The method according to the present invention can produce resin particles each of which includes a core particle and filler particles immobilized on the surface of the core particle, which core particle contains the thermoplastic resin or elastomer having one or more acidic groups. This is because the thermoplastic resin or elastomer satisfactorily interacts, through the acidic groups present in the thermoplastic resin or elastomer, with the surfaces of the filler particles. The resin particles each include the filler particles immobilized or affixed on the surface of the core particle containing the thermoplastic resin or elastomer. This structure of the resin particles can be identified, for example, by using a scanning electron microscope (SEM)

The resin particles according to the present invention having the configuration can efficiently be imparted on their surfaces with one or more desired functions or activities such as insulating properties, strength, viscosity (viscous properties), incombustibility (flame resistance), electroconductivity, brightness, coloring properties, and antimicrobial activities. The resin particles are usable, for example, as or in cosmetics (e.g., scrubbing agents and foundation); fillers; agents for imparting optical properties to resin membranes such as resin sheets and resin films; and additives.

Cosmetics according to embodiments of the present invention include resin particles produced by the method. The cosmetics may further contain common additives according to the intended use. Exemplary additives include alcohols, methylcellulose, CMC (carboxymethylcellulose), and other stabilizers, surfactants, flavors, preservatives, antioxidants, collagens, ultraviolet-absorbers, mucopolysaccharides, binders, and extending agents. Exemplary forms of the cosmetics include liquid forms such as lotions, emulsions, creams, and gels; and solid forms such as powders, granules, pastes, and molded or formed articles. Specific examples of the cosmetics include (facial) creams, foundation (foundation creams), lip creams, hand creams, body creams, toilet soaps, cleansing preparations, exfoliating cleansers, scrubbing agents, pack agents, lotions, milky lotions, beauty essences, shampoos, hair rinses (hair conditioners), and hair dressings. Among the resin particles, those using colorants as the filler are advantageously usable as foundation and other cosmetics that develop colors satisfactorily.

EXAMPLES

The present invention will be illustrated in further detail with reference to several examples below. It should be noted, however, these examples are never construed to limit the scope of the present invention. The data of the examples are shown in Table 1. In Table 1, the symbols "PA" and "PAE" as the type of resin represent a nylon 12 resin and a polyamide elastomer, respectively; and the terms "ZnO" and "TiO" as the type of filler represent zinc oxide and titanium oxide, respectively.

Example 1

In a twin-screw extruder set at 190° C. were melted and kneaded with one another 20 parts by weight of a nylon 12 resin containing 123 mmol/kg of terminal carboxyl groups, supplied by Daicel-Degussa Ltd.; as an oligosaccharide mixture, a mixture of 65 parts by weight of a powdery hydrogenated starch hydrolysate (supplied by Towa Chemical Industry Co., Ltd. under the trade name "PO-10") and 35 parts by weight of D-sorbitol; and 4 parts by weight of zinc oxide fine particles having a particle diameter of 65 nm to give a kneadate. The kneadate was extruded into strands (each about 3 mm in diameter), cooled on a belt cooler, and thereby yielded pellets of a resin composition including the polyamide 12, zinc oxide, and oligosaccharides.

Next, the pellets of resin composition were dissolved in water to a concentration of 5 percent by weight and filtrated under reduced pressure through a 5A filter paper using a suction funnel (Nutsche). This washing process (dissolving and filtrating) was repeated a total of ten times to remove the water-soluble oligosaccharides from resin particles including the polyamide and zinc oxide to thereby give a wet cake. The wet cake was dried at 80° C. under reduced pressure to give resin particles.

Figure 1:
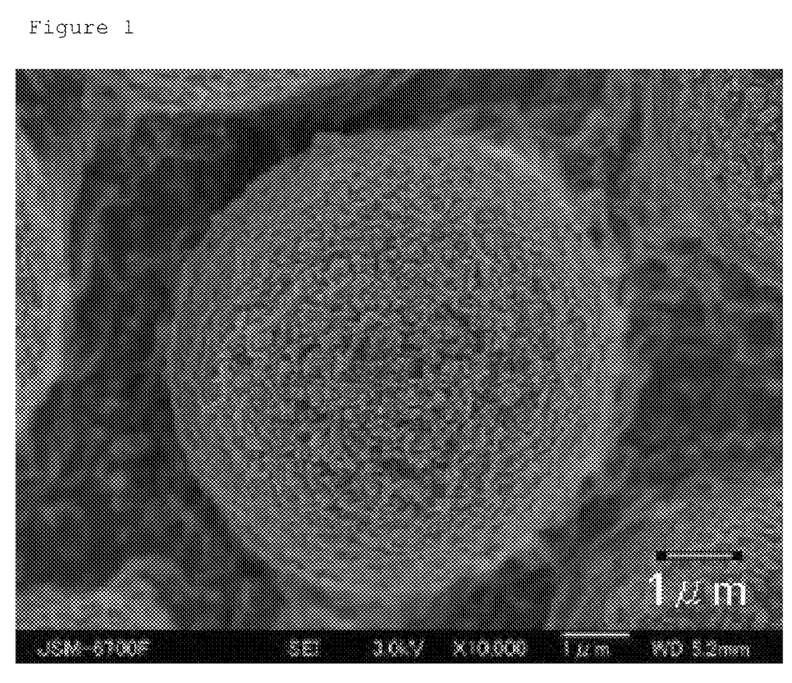
FIG. 1 is a scanning electron micrograph of resin particles prepared according to Example 1.

The prepared resin particles had a median size of 8 μm. The resin particles were observed with a scanning electron microscope (SEM) to find to be composite particles each including a polyamide core particle and zinc oxide immobilized on the outside of the polyamide core particle. A scanning electron micrograph of the resin particles is shown as FIG. 1.

Example 2

Figure 2:
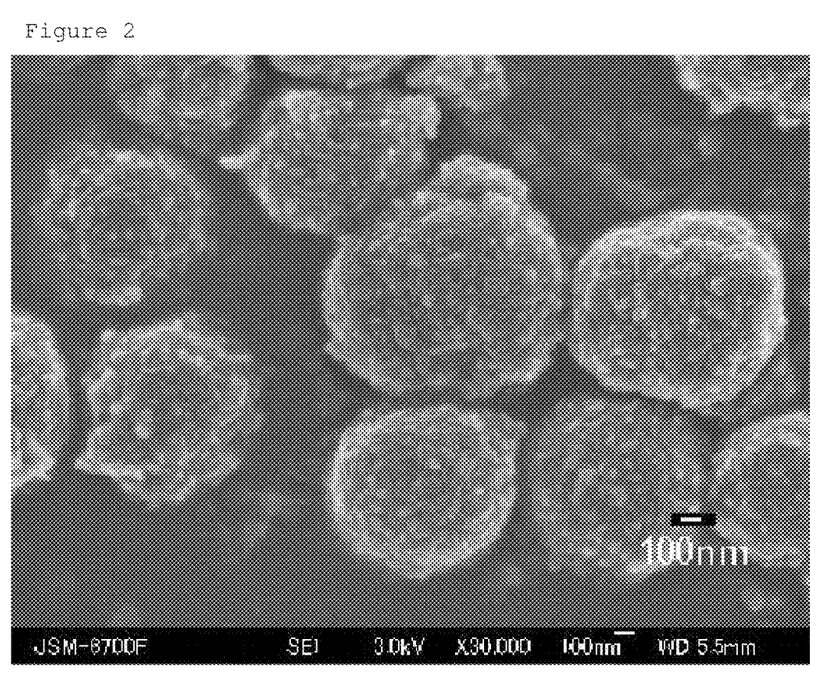
FIG. 2 is a scanning electron micrograph of resin particles prepared according to Example 2.

A resin composition was prepared, and resin particles were recovered from the resin composition by the procedure of Example 1, except for using 50 parts by weight of titanium oxide (having a particle diameter of 15 nm) instead of zinc oxide. The prepared resin particles had a median size of 1.6 μm. The resin particles were observed with a scanning electron microscope (SEM) to find to be composite particles each including a polyamide core particle and titanium oxide immobilized on the outside of the polyamide core particle. A scanning electron micrograph of the resin particles is shown as FIG. 2.

Example 3

A resin composition was prepared, and resin particles were recovered from the resin composition by the procedure of Example 1, except for using, instead of the nylon 12 resin used in Example 1, 20 parts by weight of another nylon 12 resin containing 92 mmol/kg of terminal carboxyl groups, supplied by Daicel-Degussa Ltd. The prepared resin particles had a median size of 10 μm. The resin particles were observed with a scanning electron microscope (SEM) to find to be composite particles each including a polyamide core particle and zinc oxide immobilized on the surface of the polyamide core particle.

Example 4

A resin composition was prepared, and resin particles were recovered from the resin composition by the procedure of Example 1, except for using, instead of the nylon 12 resin used in Example 1, 20 parts by weight of another nylon 12 resin containing 56 mmol/kg of carboxyl terminal groups, supplied by Daicel-Degussa Ltd. The prepared resin particles had a median size of 8 μm. The resin particles were observed with a scanning electron microscope (SEM) to find to be composite particles each including a polyamide core particle and zinc oxide immobilized on the surface of the polyamide core particle.

Example 5

A resin composition was prepared, and resin particles were recovered from the resin composition by the procedure of Example 1, except for using, instead of the nylon 12 resin used in Example 1, 20 parts by weight of a polyamide elastomer containing 19 mmol/kg of carboxyl terminal groups, supplied by Daicel-Degussa Ltd. The prepared resin particles had a median size of 32 μm. The resin particles were observed with a scanning electron microscope (SEM) to find to be composite particles each including a polyamide core particle and zinc oxide immobilized on the surface of the polyamide core particle.

Comparative Example 1

Figure 3:
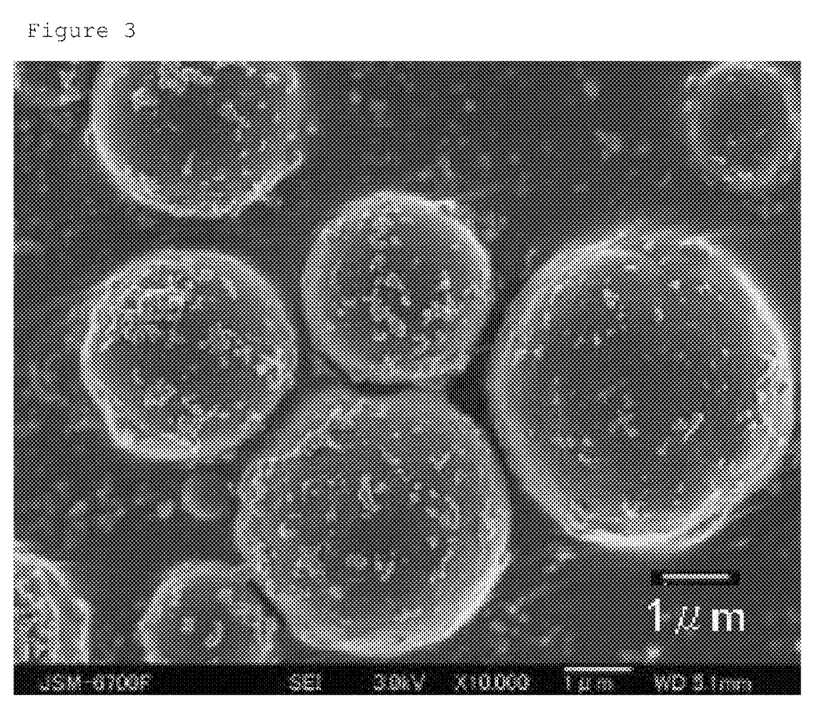
FIG. 3 is a scanning electron micrograph of resin particles prepared according to Comparative Example 1.

A resin composition was prepared, and resin particles were recovered from the resin composition by the procedure of Example 1, except for using, instead of the nylon 12 resin used in Example 1, 20 parts by weight of another nylon 12 resin containing 2 mmol/kg of terminal carboxyl groups, supplied by Daicel-Degussa Ltd. The prepared resin particles had a median size of 6 μm. The resin particles were observed with a scanning electron microscope (SEM) to find to be not composite particles each bearing zinc oxide on the surface but resin particles including polyamide particles alone. A scanning electron micrograph of the resin particles is shown as FIG. 3.

Comparative Example 2

A resin composition was prepared, and resin particles were recovered from the resin composition by the procedure of Example 1, except for using, instead of the nylon 12 resin used in Example 1, 20 parts by weight of a polyamide elastomer containing 3 mmol/kg of terminal carboxyl groups, supplied by Daicel-Degussa Ltd. The prepared resin particles had a median size of 27 μm. The resin particles were observed with a scanning electron microscope (SEM) to find to be not composite particles each bearing zinc oxide on the surface but resin particles including polyamide particles alone.

TABLE 1

|  |  | Examples | | | | | Comparative Examples | |
|---|---|---|---|---|---|---|---|---|
|  |  | 1 | 2 | 3 | 4 | 5 | 1 | 2 |
| Resin | Type | PA | PA | PA | PA | PAE | PA | PAE |
|  | Amount of terminal carboxyl groups [mmol/kg] | 123 | 123 | 92 | 56 | 19 | 2 | 3 |
| Filler | Type | ZnO | TiO | ZnO | ZnO | ZnO | ZnO | ZnO |
|  | Particle diameter [nm] | 65 | 15 | 65 | 65 | 65 | 65 | 65 |
| median size of resin particles [μm] |  | 8 | 1.6 | 10 | 8 | 32 | 6 | 27 |

INDUSTRIAL APPLICABILITY

The method according to the present invention enables efficient and simple production of fine particles (outer-bearing fine particles) each including a resin fine core particle and, immobilized on the outside thereof, an inorganic pigment. This is achieved by preparing a resin composition including a matrix water-soluble material, and resin fine particles dispersed in the matrix; and removing the water-soluble material from the resin composition. The outer-bearing fine particles readily exhibit high-value-added functions which the inorganic fine particles inherently have. Thus, resin particles usable in a wide variety of applications can be provided by using inorganic fine particles having desired properties or functions.

The invention claimed is:

1. A method for the production of resin particles, the method comprising the steps of
   melting and mixing a thermoplastic resin or elastomer having one or more carboxyl groups or carboxylic anhydride groups with filler particles and a water-soluble material to form a resin composition, the resin composition including a matrix and resin fine particles dispersed in the matrix, the resin fine particles formed from the thermoplastic resin or elastomer and the filler particles, and the matrix formed from the water-soluble material; and
   removing the matrix component from the resin composition to give the resin particles, wherein the amount of carboxyl groups and carboxylic anhydride groups in the thermoplastic resin or elastomer before mixing and kneading step is 5 mmol/kg or more based on the total amount of the thermoplastic resin or elastomer, and the resulting resin particles each include the filler particles immobilized on the surface of the resin particle to produce a core-shell structure wherein the core comprises the resin particle and the shell comprises the filler particles;
   wherein the water-soluble material is selected from the group consisting of monosaccharides, oligosaccharides, sugar alcohols, polydextroses, maltodextrins, inulins; hydrates and hydrolysates thereof;

the removing step comprising: dissolving the pellets of resin composition in water, water-soluble organic solvents, or mixtures thereof; filtrating the resulting solution of resin composition under reduced pressure; repeating the washing process including dissolving and filtrating to remove the water-soluble material and to give a wet cake; and drying the wet cake under reduced pressure to give resin particles, wherein the thermoplastic resin or elastomer having one or more carboxyl groups or carboxylic anhydride groups is selected from polyamide resins and polyamide elastomers.

2. The method for the production of resin particles, according to claim 1, wherein the filler particles have a particle size of from 0.001 to 100 μm, and wherein the resulting resin particles have a particle size of from 0.5 to 80 μm.

3. The method for the production of resin particles, according to claim 1, wherein the filler particles have been treated with a surface treating agent containing a basic group.

4. The method for the production of resin particles, according to claim 1, wherein the filler particles are inorganic fillers selected from the group consisting of calcium carbonate, magnesium carbonate, clay, kaolin, calcium phosphate, hydroxyapatite, mica, talc, silica, quartz powder, glass powder, diatomaceous earth, nepheline syenite, cristobalite, wollastonite, aluminum hydroxide, iron oxide, zinc oxide, titanium oxide, aluminum oxide, calcium sulfate, barium sulfate, dolomite, silicon carbide, silicon nitride, boron nitride, metallic powders, graphite, and carbon black.

5. The method for the production of resin particles according to claim 3, wherein the surface treating agent is a silane coupling agent.

6. The method for the production of resin particles according to claim 1, wherein the water-soluble material has a viscosity as low as possible when dissolved in a disperse medium.

7. The method for the production of resin particles according to claim 6, wherein the disperse medium is water.

8. Resin particles produced by the method of any one of claims 1, 2, 3, 4, or 5.

9. A cosmetic comprising the resin particles of claim 8.

* * * * *